United States Patent
Stange et al.

(10) Patent No.: US 6,426,373 B1
(45) Date of Patent: Jul. 30, 2002

(54) PHOTOPOLYMERIZABLE ONE-COMPONENT DENTAL MATERIAL

(75) Inventors: Frank Stange, Westerfelder; Albert Erdrich, Schnurstrasse; Novica Savic, Dietrich Bonhoefer; Teresa Puchalska, Theodor-Heuss-Strasse, all of (DE)

(73) Assignee: Heraeus Kulzer GmbH & Co. KG, Hanau (DE)

( * ) Notice: Subject to any disclaimer, the term of this patent is extended or adjusted under 35 U.S.C. 154(b) by 0 days.

(21) Appl. No.: 09/373,302

(22) Filed: Aug. 12, 1999

(30) Foreign Application Priority Data

Oct. 23, 1998 (DE) .......................................... 198 48 886

(51) Int. Cl.⁷ ............................................... A61K 6/083
(52) U.S. Cl. ................. 523/116; 523/115; 433/37; 433/40; 433/48; 433/202.1; 433/228.1; 522/27; 522/28; 522/30; 522/64; 522/65; 522/68; 522/96; 522/102; 522/103; 522/908; 526/318.42; 526/318.43; 526/318.44
(58) Field of Search ............................. 433/37, 40, 48, 433/202.1, 228.1; 522/27, 28, 30, 64, 65, 68, 96, 102, 103, 908; 523/115, 116; 526/318.42, 318.43, 318.44

(56) References Cited

U.S. PATENT DOCUMENTS

| 4,656,053 A |   | 4/1987 | Angrick et al. ............. 427/53.1 |
| 4,740,159 A | * | 4/1988 | Hamilton et al. ............. 433/37 |
| 5,430,074 A | * | 7/1995 | Barnes et al. ................ 523/115 |
| 5,444,104 A | * | 8/1995 | Waknine ..................... 523/116 |
| 5,684,103 A |   | 11/1997 | Jia et al. .................. 526/218.1 |
| 5,969,000 A | * | 10/1999 | Yang et al. ................. 523/116 |

FOREIGN PATENT DOCUMENTS

| DE | 3404904 A1 | 8/1985 |
| DE | 4005 570 A1 | 8/1991 |
| DE | 195 02 751 A1 | 8/1996 |
| EP | 0 070 634 A2 | 1/1983 |
| EP | 0 142 172 A2 | 5/1985 |
| WO | WO 96/15179 | 5/1996 |

OTHER PUBLICATIONS

Taschenbuch der Zahnärztlichen Werkstoffkunde, 4., neu bearbeitete Auglage von H. Meiners, Mit 151 Abbildungen, Carl Hanser Verlag München Wien, pp. 110–111.

* cited by examiner

Primary Examiner—Peter Szekely
(74) Attorney, Agent, or Firm—Norris McLaughlin & Marcus

(57) ABSTRACT

Among other things, a photopolymerizing one-component dental material is prepared, containing:

1) 80–10 weight-% of at least one polyfunctional urethane methacrylate and/or at least one polyfunctional urethane acrylate,
2) 10–30 weight-% of at least one polyfunctional acrylate resin,
3) 10–30 weight-% of at least one reactive thinner,
4) 0–20 weight-% of bis-GMA and/or at least one ethoxylated bisphenol-A-dimethacrylate,
5) 0–10 weight-% of at least one filler,
6) 0–1 weight-% of at least one photoinitiator, and.
7) 0–1 weight-% of at least one color pigment.

61 Claims, No Drawings

PHOTOPOLYMERIZABLE ONE-COMPONENT DENTAL MATERIAL

The invention relates to a photopolymerizable one-component dental material, a dental kit, a method of making a prosthesis, the use of such dental material, a corresponding prosthesis, a fixing key, another dental kit, another method of making prostheses, the use of a specific material as fixing key and lastly an additional prosthesis.

The systems mainly used on the dental market for restoration are two-component systems on a powder-and-liquid basis, which can be worked by casting methods or by packing and pressing methods. Curing is performed by hardening in the water bath or in the microwave oven, and often pressure is applied to the restoration structures that are formed, especially prostheses, to prevent ebullition bubbles.

A disadvantage of this is the necessity of mixing so that, if too much material is mixed, it has to be discarded. Furthermore, these systems contain methyl methacrylate (MMA) and peroxides which have a high potential for irritation. Furthermore, the working time is as a rule very limited due to the swelling of the polymers and by the reaction start in autopolymerizates.

Far less widely used are the one-component systems, which heretofore have been used mainly for the full prosthesis market. These systems contain thermosetting, dough-like materials, with the result that casting them is not possible and—as is common practice with full prostheses—embedding in plaster must be performed.

Furthermore, the polymerization is very slow and the cooling phase that follows it is disproportionately long. The plastic dough contains as a rule, and in a disadvantageous manner, peroxide as the initiator which, as mentioned above, has a high irritation potential. The post-curing, especially in the case of glass-filled systems, is very time-consuming, and furthermore affinity for plaque accumulation is very great. Lastly, the materials' technical properties are unsatisfactory as a rule due to poor bonding of the fillers.

From what is set forth above, the problem arises of at least partially remedying the disadvantages named above by means of a new one-component dental material and, among other things, a new dental kit. The problem lies especially in devising a one-component dental material and a corresponding kit in which the production time is definitely shorter in comparison to the usual methods and materials, no free methyl methacrylate and virtually no peroxide is used, bonding to commercial polymethyl methacrylate (PMMA) materials is possible, and lastly the fettling that follows polymerization should be similar as regard difficulty to the systems of the prior art.

This problem is solved according to the invention by a one-component dental material comprising:
a) 80–10 weight-% of at least one polyfunctional urethane methacrylate and/or at least one polyfunctional urethane acrylate,
b) 10–30 weight-% of at least one polyfunctional acrylate resin,
c) 10–30 weight-% of at least one reactive thinner,
d) 0–20 weight-% of bis-GMA and/or at least one ethoxylated bisphenol-A dimethacrylate,
e) 0–10 weight-% of at least one filler,
f) 0–1 weight-% of at least one photoinitiator system, and
g) 0–1 weight-% of at least one color pigment.

The invention furthermore relates to a dental kit comprising the inventive one-component dental material; to a method for making a prosthesis, wherein the inventive one-component dental material is used; to a prosthesis comprising the inventive one-component dental material; to a fixing key comprising at least one transparent silicone or composite; to a dental kit comprising the inventive fixing key; to a method for making a prosthesis, wherein the inventive fixing key is used; and to a prosthesis comprising the inventive fixing key.

The one-component dental material according to the invention is one which has at least one polyfunctional urethane methacrylate and/or at least one polyfunctional urethane acrylate, at least one polyfunctional acrylate resin and at least one reactive thinner. The term, "reactive thinner," as used in the context of the invention is to be understood as compounds which act more or less as "solvents and thinners" in their monomeric form, and thus reduce the viscosity of the one-component dental material, and furthermore which become copolymerized in the polymer matrix when it is set by exposure to light, i.e., when it is polymerized by wavelengths of light.

Furthermore, the material according to the invention can contain bis-GMA and/or at least one ethoxylated bisphenol A dimethacrylate which has positive influence on such material parameters as shrinkage, moisture absorption and mechanical properties. Bis-GMA is the common abbreviation of 2,2-bis(4-(2-hydroxy-3-methacryloyloxypropoxy)phenyl)propane and has the following structural formula:

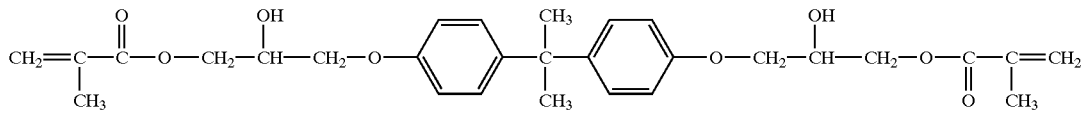

Lastly, fillers, photoiniator systems and color pigments can be components of the material. The fillers can be hydrophobized—silanized for example, which improves wettability due to the lower polar character, which leads to easier copolymerizability into the matrix. Methacryloyloxypropyl-trimethoxy-silane is named as one example of many.

The photoinitiator system can consist, for example, of individual photoinitiators or else of systems which contain photoinitiators and co-initiators.

The color pigments can be of an organic nature, on a perylene basis for example, or of an inorganic nature, on a spinel basis for example.

Urethane methacrylate is the product of the reaction of a diisocyanate with an OH-functional methacrylate such as hydroxyethyl methacrylate for example. When a diisocyanate is used, the product is a urethane dimethacrylate; if an OH-functional acrylate is used, such as a hydroxyethyl acrylate, a difunctional acrylate is the result, similarly to the methacrylate.

Such a urethane methacrylate or urethane acrylate, especially a urethane dimethacrylate is advantageous, because among other things it offers superior material properties such as great stiffness or low moisture absorption.

Also possible is the use of a monomer prepared from the combination of triisocvanates or higher isocyanates with OH-functional acrylates or methacrylates, in which case these urethane methacrylates or urethane acrylates will have a functionality of 3 or more.

Advantageously, the urethane methacrylate is a urethane dimethacrylate or urethane trimethacrylate and the urethane acrylate is a urethane diacrylate or a urethane triacrylate.

It is furthermore advantageous if the urethane methacrylate and/or urethane acrylate has a viscosity of $10^3$ to $5\times10^4$ mPas, especially $1\times10^4$ mPas, since when used in the one-component dental material as the main monomer, even without dilution, a good consistency for the dental plastic according to the invention is obtained. Advantageously, the urethane methacrylate and/or urethane acrylate has at $T=+20°$ C. a viscosity of $10^3$ to $5\times10^4$ mPas.

Advantageously, the urethane methacrylate and/or the urethane acrylate has a molar mass of 450 to 500 g/mol, since the shrinkage of the monomer is in the range of normal prosthesis materials. For example, the shrinkage of the monomer at a functionality of 2 (i.e., a urethane dimethacrylate or a urethane diacrylate) is less than 7%.

It is advantageous if the urethane methacrylate and/or the urethane acrylate is aliphatic, since such urethane methacrylates have a lower discoloration especially when irradiated with light containing UV than do aromatic urethane methacrylates and urethane acrylates.

The following urethane methacrylate of the following structural formula: has proven practical.

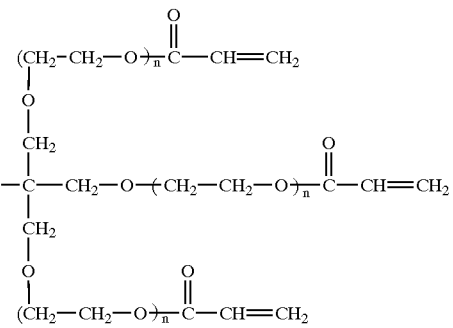

It is advantageous that the acrylate resin is a polyester triurethane acrylate, since due to a functionality of 3 a great stiffness results in spite of the high molar mass; and it is characterized by the elasticity modulus. Due to the long chains between the functional groups a high flexibility is simultaneously achieved, which leads to a decided improvement in impact toughness.

Advantageously, at $T=+60°$ C., the acrylate resin has a viscosity of 5,000 to 15,000 mPas, since the high viscosity of this monomer permits good adjustment of the viscosity of the mixture through variation with reactive thinners and the main monomer (polyfunctional urethane methacrylate or urethane acrylate).

Advantageously, the reactive thinner is selected from:

TRIM: Trimethylol propane trimethacrylate:

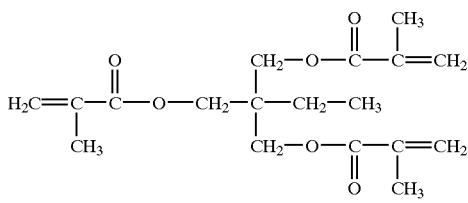

or:

TEDMA: Triethylene glycol dimethacrylate:

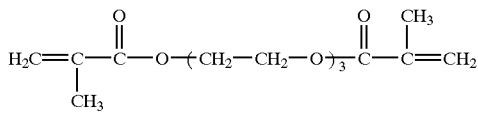

or:

Pentaerythritol tetraacrylate: average n=2–3:

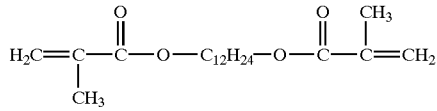

or:

DDMA: Dodecanediol dimethacrylate:

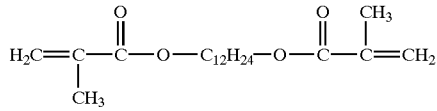

or:

Isobornyl methacrylate:

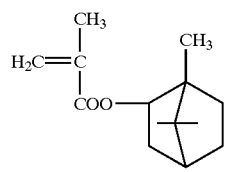

It has proven especially beneficial if the acrylate resin has a molar mass of 1,000 to 1,200 g/mol, since due to the high molar mass a good shrinkage of less than 5% occurs during polymerization.

Furthermore, it is advantageous if the ethoxylated bisphenol-A-dimethacrylate has the structural formula:

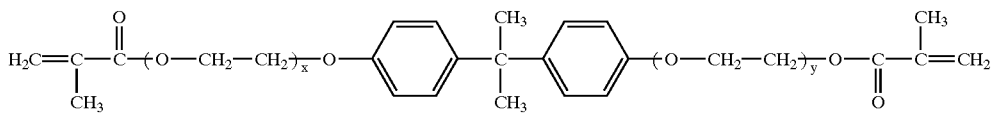

wherein the indices X and Y of the structural formula are in the range of 1 to 4, since bis-GMA as well as the corresponding ethoxylated bisphenol-A dimethacrylates are characterized by low shrinkage and good mechanical properties, the latter compounds furthermore having very little moisture absorption and solubility in water.

Advantageously, the photoinitiator system contains:

2,4,6-trimethylbenzoyl diphenyl phosphinic oxide (TMDPO):

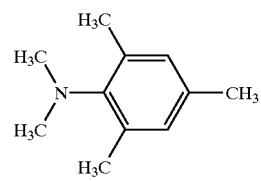

and/or 2-hydroxy-2-methyl-1-phenylpropane-1-one:

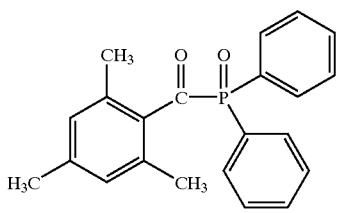

and/or 2,3-bornanedione:

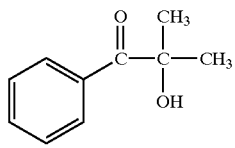

and/or 2-n-butoxyethyl-4-dimethylaminobenzonate:

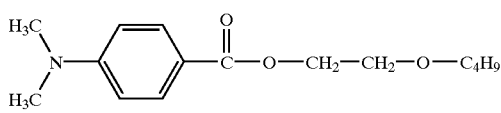

and/or

PMA: pentamethyl aniline:

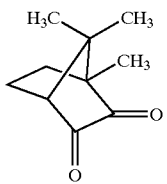

Advantageously, the color pigment is an organic perylene, a titanium dioxide or a cobalt zinc aluminate blue spinel pigment.

Advantageously, the use of silicon dioxide, and especially the use of highly disperse pyrogenic silicic acids as fillers, permits precise setting of the flow characteristics with stationary behavior at rest and flow under stresses such as stirring and pouring (thixotropic effects). The use of silanized filler not only improves wettability by lowering the polar character, but also achieves a chemical binding into the matrix. Such a filler acts as an additional crosslinking agent and increases stiffness. An example of a silane polymerized into the matrix is, for example, methacryloyloxypropyl trimethoxy silane.

Another important element inherent in the invention is a fixing key for the making of prostheses, which contains a transparent silicone or composite.

In the context of the invention, the term "composite" is to be understood to mean a photopolymerizing one-component material filled with inorganic fillers, such as glass, or organic fillers.

Also in the context of the invention, the term "fixing key" is to be understood to mean an atleast partially cured material which serves for fixing the position of the individual teeth.

Of decisive importance to the invention is the fact that a fixing key is involved which is transparent in the light wavelength range used for the polymerization of the dental material according to the invention.

In the fixing key consisting of silicone it is advantageous if the silicone has a Shore A hardness of 50 to 80 and is a crosslinking vinyl polysiloxane, since the latter has a high transparency, sets rapidly at room temperature without technical aids, and has a high stripping accuracy in setting up the teeth in the wax. Due to the chemical incompatibility of silicone with methacrylates and acrylates, even without parting agents, no adhesion occurs between the plastic of the prosthesis and the fixing key.

Furthermore, it is advantageous if the composite is a light-cured polymer filled with glass or organic fillers, since it combines high mechanical stiffness with high transparency. In this case, however, an additional parting agent is needed to insulate the plastic of the prosthesis from the composite.

The two dental kits according to the invention contain at least one dental material according to the invention, or at least one transparent, crosslinking silicone or composite as fixing key, such a kit advantageously containing both the dental material and the fixing key material.

Furthermore, such a kit can contain a photopolymerizing adhesive for bonding the artificial teeth to the prosthesis, a cover material such-as a lacquer or a gel-like paste to prevent dispersion layers due to air, and a lacquer containing an initiator to improve polymerization at points inaccessible to light.

The dental material as such can be transparent as well as dyed in popular prosthesis colors and veined. Veining is to be understood to mean the addition of plastic fibers (length up to 2 mm) to the already dyed material in order to achieve an appearance as natural as possible in the polymerized material. The oxygen of the air can cause inhibition of the polymerization reaction with the formation of air-related dispersion layers, so that after the polymerization a thin, unpolymerized layer would remain on the surface of the plastic, bu this can be prevented by the above-mentioned cover material.

The dental material can be offered for sale in cartridges, syringes or tubes. When processed it has thixotropic characteristics, i.e., brief flowing under pressure or when worked, but then becoming stiff. However, polymerization layer by layer, especially by hand-held lighting devices, is possible.

Shrinkage is minimized by the use of exclusively polyfunctional monomers, especially those of high molecular weight. This makes it possible to get by without large amounts of filler while still keeping shrinkage within the range of that of normal two-component casting plastics (about 7%). Refraining from larger amounts of fillers avoids the problem of the bonding of the monomer matrix to the fillers. If harder fillers, such as glass etc., are used, workability (grinding, polishing) is similar to that of conventional materials. The greater brittleness that occurs when polyfunctional monomers are used is compensated by acrylate resin, especially acrylate resin of high molecular weight. Fabrication is performed as usual by casting, but curing is performed by exposure to light, for example by irradiation with stroboscope lamps, which is for the first time made possible by the use of transparent fixing keys. The avoidance of the preparatory mixing process furthermore assures an always uniform working consistency and unvarying properties of the material.

Applications beyond the preparation of prostheses are, for example, the lining of full dentures, the repair of full and partial prostheses and orthodontic applications. With transparent embedding material extension into the field of total prosthetics is quite possible.

The dental material properties satisfy ISO 1567. Samples thus far have shown an elasticity modulus of about 2200 MPa and a flexural strength of about 85 MPa, the impact strength (DIN 53435) was greater than 6 kJ/m$^2$.

The method, prostheses and applications according to the invention likewise have the above-stated surprising and beneficial properties.

The following example serves to explain the invention.

As the first step in providing a toothless person with full dentures a functional impression of the jaws is performed. The impression making materials used today are generally alginates which are supplied in powder form and mixed with water to form a paste. By adding other materials a poorly soluble, crosslinked gel is formed. The partially crosslinked gel is applied to the area of the teeth of the patient and thus an impression is made. Materials on a silicone basis can also be used like the alginate as an impression taking medium.

By casting in the impression, which constitutes a negative mold, a positive is obtained, the working model. Plaster is used almost exclusively as the modeling material.

1. Preliminary work

The teeth are set up in wax on the plaster working model. The wax serves to hold them in place for the plastic—the dental material. The silicone mixed to create the fixing key is fitted to this wax setup. The two-component silicone material mixes by itself when squeezed out and sets within 3 to 5 minutes. After the silicon is set the fixing key is removed, the wax is removed and the teeth are fastened in the silicone fixing key. The latter is them placed again on the plaster model. Metal frames later to be incorporated during polymerization are normally prepared by sandblasting, conditioning and then coating with Opaker, i.e., an opaque, color-toned metal covering lacquer.

2. Preparation of the model

Alginate insulation is brushed onto the moist plastic model in two thin coats and then air-dried. The alginate insulation separates the water contained in the plastic from the plastic and furthermore seals the pores of the plaster. In this manner the so-called white discoloration caused by water deposited in the fully polymerized plastic is effectively suppressed. The application of a coating containing initiator to assist the later photopolymerization is advantageous because of hold-outs at places that are poorly accessible to light.

3. Conditioning the teeth and metal frames

The basal surfaces of the teeth are roughened with a diamond grinder and then conditioned with an adhesive agent, consisting for example of a light-initiated methacrylate of low molecular weight. In contrast to normal powder-and-liquid systems, this adhesive agent is hardened by light to assure an optimum bond when the polymerization is performed. Especially the backs of the metal frames which are poorly irradiated are coated with a monomer coating containing initiator to assist curing, consisting for example of more greatly initiated base dental materials or materials containing slight amounts of peroxide.

4. Using the casting plastic

The ready-to-use casting plastic in a cartridge or tube, i.e., the actual dental material, is directly cast into the space between the plaster and the front wall of silicone (the fixing key). In contrast to commercial systems, the mixing—the embedding in the case of paste-like materials, can be avoided. In the case of extremely thickpieces, or else in the case of opaque colors, it may be necessary to polymerize the plastic layer by layer. The plastic is relatively immobile after casting due to thixotropy, but it can be polymerized superficially with a manual lighting tool to fix it.

Then follows polymerization by flash light, and after the first polymerization the silicone front wall is removed in order then to be exposed again to light. Before the second, merely optional light exposure, exposed plastic surfaces are coated with . antidispersion gel to avoid the inhibition layer. This gel can contain, for example, a glycerin and water basis.

5. Finishing

Finishing is performed as a rule by grinding and polishing.

What is claimed is:

1. A Photopolymerizable one-component dental material comprising:

a) 80–10 weight-% of at least one polyfunctional urethane methacrylate and/or at least one polyfunctional urethane acrylate, b) 10–30 weight-% of at least one polyester triurethane acrylate, c) 10–30 weight-% of at least one reactive thinner, d) 0–20 weight-% of 2,2-bis(4-(2-hydroxy-3-methacryloyloxypropoxy)phenyl)propane (bis-GMA) and/or at least one ethoxylated bisphenol-A dimethacrylate, e) 0–10 weight-% of at least one filler, f) 0–1 weight-% of at least one photoinitiator system, and g) 0–1 weight-% of at least one color pigment.

2. Dental material according to claim 1, wherein the urethane methacrylate is a urethane dimethacrylate or urethane trimethacrylate and the urethane acrylate is a urethane diacrylate or a urethane triacrylate.

3. Dental material according to claim 1, wherein the urethane methacrylate and/or urethane acrylate has at T=+20° C. a viscosity of $10^3$ to $5\times10^4$ mPas.

4. Dental material according to claim 1, wherein the urethane methacrylate and/or urethane acrylate has a molar mass of 450 to 500 g/mol.

5. Dental material according to claim 1, wherein the urethane methacrylate and/or urethane acrylate is aliphatic.

6. Dental material according to claim 1, wherein the urethane methacrylate has the following structural formula:

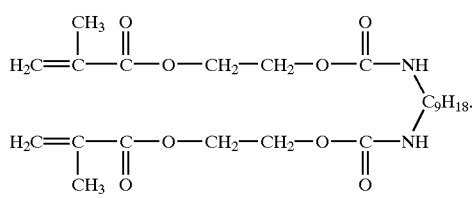

7. Dental material according to claim 1, wherein the acrylate resin has a viscosity of 5000 to 15000 mPas at T=+60° C.

8. Dental material according to claim 1, wherein the acrylate resin has a molar mass of 1000 to 1200 g/mol.

9. Dental material according to claim 1, wherein the reactive thinner is selected from the group consisting of:

a) Trimethylol propane trimethacrylate (TRIM);

b) Triethylene glycol dimethacrylate (TEDMA);

c) Pentaerythritol tetraacrylate of the formula:

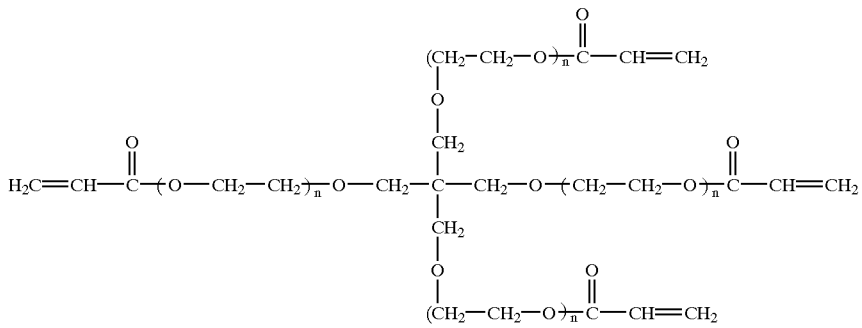

wherein on average n=2–3;

d) Dodecanediol dimethacrylate (DDMA); and e) Isobornyl methacrylate.

10. Dental material according to claim 1, wherein the ethoxylated bisphenol-A-dimethacrylate has the following structural formula, wherein the indices X and Y of the structural formula range from 1 to 4:

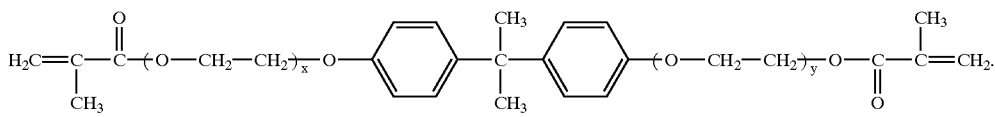

11. Dental material according to claim 1, wherein the filler comprises silicon dioxide.

12. Dental material according to claim 11, wherein the filler contains pyrogenic silicic acids.

13. Dental material according to claim 1, wherein the photoinitiator system comprises one or more members selected from the group consisting of:

a) 2,4,6-trimethylbenzoyl diphenyl phosphinic oxide (TMDPO);

b) 2-hydroxy-2-methyl-1-phenylpropane-1-one;

c) 2,3-bomanedione;

d) 2-n-butoxyethyl-4-dimethylaminobenzonate; and e) pentamethyl aniline (PMA).

14. Dental material according to claim 1, wherein the color pigment is an organic perylene, a titanium dioxide or a cobalt zinc aluminate blue spinel pigment.

15. Dental kit containing at least one dental material according to claim 1.

16. Dental kit according to claim 15, containing at least one transparent, crosslinking silicone or composite as fixing key.

17. Dental kit according to claim 16, wherein the silicone has a Shore A hardness of 50 to 80.

18. Dental kit according to claim 16, wherein the silicone is a crosslinking vinyl polysiloxane.

19. Dental kit according to claim 16, wherein the composite is a photocrosslinking polymer filled with glass or organic fillers.

20. Method for making a prosthesis, wherein a dental material according to claim 1 is used.

21. Photopolymerizable one-component dental material comprising:

a) 80–10 weight-% of at least one polyfunctional urethane methacrylate and/or at least one polyfunctional urethane acrylate, b) 10–30 weight-% of at least one polyfunctional acrylate resin having a viscosity of 5000 to 15000 mPas at T=+60° C., c) 10–30 weight-% of at least one reactive thinner, d) 0–20 weight-% of 2,2-bis(4-(2-hydroxy-3-methacryloyloxypropoxy)phenyl)propane (bis-GMA) and/or at least one ethoxylated bisphenol-A dimethacrylate, e) 0–10 weight-% of at least one filler, f) 0–1 weight-% of at least one photoinitiator system, and g) 0–1 weight-% of at least one color pigment.

22. Dental material according to claim 21, wherein the urethane methacrylate is a urethane dimethacrylate or urethane trimethacrylate and the urethane acrylate is a urethane diacrylate or a urethane triacrylate.

23. Dental material according to claim 21, wherein the urethane methacrylate and/or urethane acrylate has at T=+20° C. a viscosity of $10^3$ to $5 \times 10^4$ mPas.

24. Dental material according to claim 21, wherein the urethane methacrylate and/or urethane acrylate has a molar mass of 450 to 500 g/mol.

25. Dental material according to claim 21, wherein the urethane methacrylate and/or urethane acrylate is aliphatic.

26. Dental material according to claim 21, wherein the urethane methacrylate has the following structural formula:

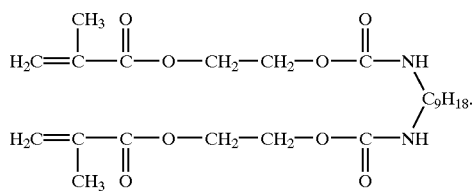

27. Dental material according to claim 21, wherein the acrylate resin has a molar mass of 1000 to 1200 g/mol.

28. Dental material according to claim 21, wherein the reactive thinner is selected from the group consisting of:

a) Trimethylol propane trimethacrylate (TRIM);

b) Triethylene glycol dimethacrylate (TEDMA);

c) Pentaerythritol tetraacrylate of the formula:

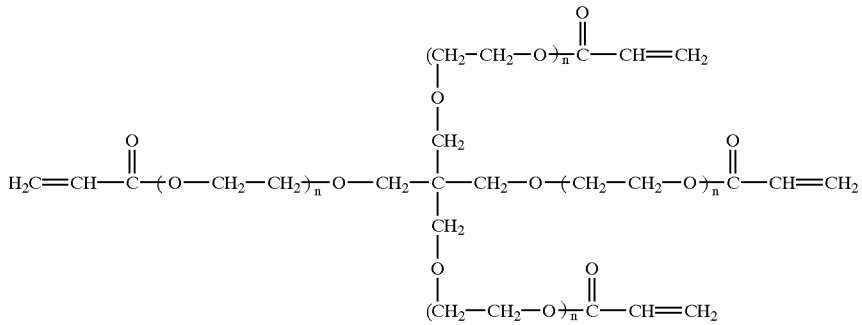

wherein on average n=2–3;

d) Dodecanediol dimethacrylate (DDMA); and e) Isobornyl methacrylate.

29. Dental material according to claim 21, wherein the ethoxylated bisphenol-A-dimethacrylate has the following structural formula, wherein the indices X and Y of the structural formula range from 1 to 4:

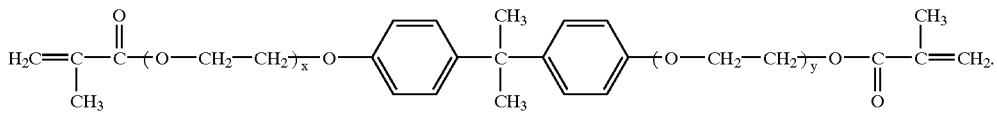

30. Dental material according to claim 21, wherein the filler comprises silicon dioxide.

31. Dental material according to claim 30, wherein the filler contains pyrogenic silicic acids.

32. Dental material according to claim 21, wherein the photoinitiator system comprises one or more members selected from the group consisting of:

a) 2,4,6-trimethylbenzoyl diphenyl phosphinic oxide (TMDPO);

b) 2-hydroxy-2-methyl-1-phenylpropane-1-one;

c) 2,3-bornanedione;

d) 2-n-butoxyethyl-4-dimethylaminobenzonate; and e) pentamethyl aniline (PMA).

33. Dental material according to claim 21, wherein the color pigment is an organic perylene, a titanium dioxide or a cobalt zinc aluminate blue spinel pigment.

34. Dental kit containing at least one dental material according to claim 21.

35. Dental kit according to claim 34, containing at least one transparent, crosslinking silicone or composite as fixing key.

36. Dental kit according to claim 35, wherein the silicone has a Shore A hardness of 50 to 80.

37. Dental kit according to claim 35, wherein the silicone is a crosslinking vinyl polysiloxane.

38. Dental kit according to claim 35, wherein the composite is a photocrosslinking polymer filled with glass or organic fillers.

39. Method for making a prosthesis, wherein a dental material according to claim 21 is used.

40. Photopolymerizable one-component dental material comprising:

a) 80–10 weight-% of at least one polyfunctional urethane methacrylate and/or at least one polyfunctional urethane acrylate, b) 10–30 weight-% of at least one polyfunctional acrylate resin having a molar mass of 1000 to 1200 g/mol, c) 10–30 weight-% of at least one reactive thinner, d) 0–20 weight-% of 2,2-bis(4-(2-hydroxy-3-methacryloyloxypropoxy)phenyl)propane (bis-GMA) and/or at least one ethoxylated bisphenol-A dimethacrylate, e) 0–10 weight-% of at least one filler, f) 0–1 weight-% of at least one photoinitiator system, and g) 0–1 weight-% of at least one color pigment.

41. Dental material according to claim 40, wherein the urethane methacrylate is a urethane dimethacrylate or urethane trimethacrylate and the urethane acrylate is a urethane diacrylate or a urethane triacrylate.

42. Dental material according to claim 40, wherein the urethane methacrylate and/or urethane acrylate has at T=+20° C. a viscosity of $10^3$ to $5 \times 10^4$ mPas.

43. Dental material according to claim 40, wherein the urethane methacrylate and/or urethane acrylate has a molar mass of 450 to 500 g/mol.

44. Dental material according to claim 40, wherein the urethane methacrylate and/or urethane acrylate is aliphatic.

45. Dental material according to claim 40, wherein the urethane methacrylate has the following structural formula:

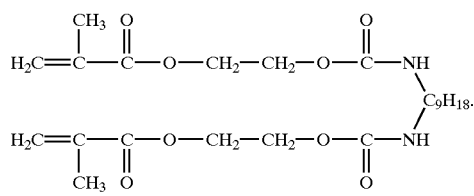

46. Dental material according to claim 40, wherein the reactive thinner is selected from the group consisting of:

a) Trimethylol propane trimethacrylate (TRIM);

b) Triethylene glycol dimethacrylate (TEDMA);

c) Pentaerythritol tetraacrylate of the formula:

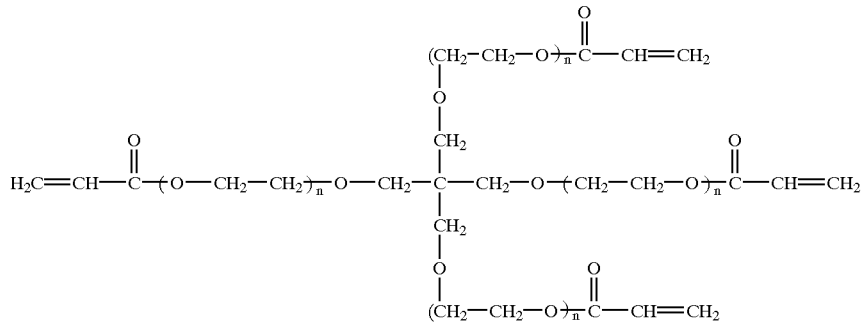

where on average n=2–3;

d) Dodecanediol dimethacrylate (DDMA); and e) Isobornyl methacrylate.

47. Dental material according to claim 40, wherein the ethoxylated bisphenol-A-dimethacrylate has the following structural formula, wherein the indices X and Y of the structural formula range from 1 to 4:

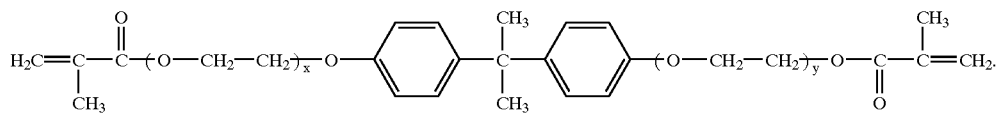

48. Dental material according to claim 40, wherein the filler comprises silicon dioxide.

49. Dental material according to claim 48, wherein the filler contains pyrogenic silicic acids.

50. Dental material according to claim 40, wherein the photoinitiator system comprises one or more members selected from the group consisting of:

a) 4,6-trimethylbenzoyl diphenyl phosphinic oxide (TMDPO);

b) 2-hydroxy-2-methyl-1-phenylpropane-1-one;

c) 2,3-bornanedione;

d) 2-n-butoxyethyl-4-dimethylaminobenzonate; and/or e) pentamethyl aniline (PMA).

51. Dental material according to claim 40, wherein the color pigment is an organic perylene, a titanium dioxide or a cobalt zinc aluminate blue spinel pigment.

52. Dental kit containing at least one dental material according to claim 40.

53. Dental kit according to claim 52, containing at least one transparent, crosslinking silicone or composite as fixing key.

54. Dental kit according to claim 53, wherein the silicone has a Shore A hardness of 50 to 80.

55. Dental kit according to claim 53, wherein the silicone is a crosslinking vinyl polysiloxane.

56. Dental kit according to claim 53, wherein the composite is a photocrosslinking polymer filled with glass or organic fillers.

57. Method for making a prosthesis, wherein a dental material according to claim 40 is used.

58. Dental kit containing:

a) at least one transparent, crosslinking silicone or composite as fixing key; and b) at least one photopolymerizable one-component dental material comprising:

1) 80–10 weight-% of at least one polyfunctional urethane methacrylate and/or at least one polyfunctional urethane acrylate, 2) 10–30 weight-% of at least one polyfunctional acrylate resin, 3) 10–30 weight-% of at least one reactive thinner is selected from:

i) Trimethylol propane trimethacrylate (TRIM);
ii) Triethylene glycol dimethacrylate (TEDMA);
iii) Pentaerythritol tetraacrylate of the formula:

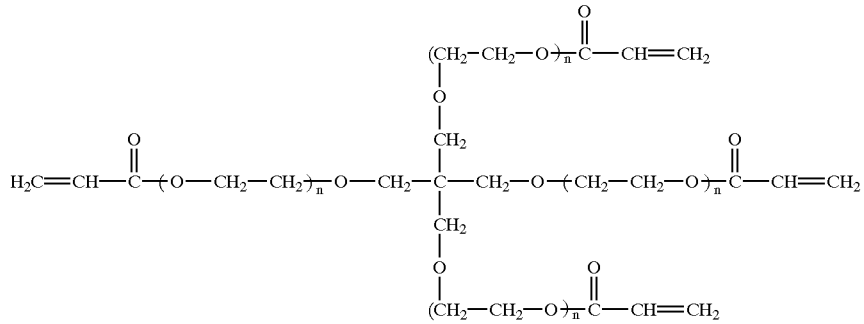

wherein on average n=2–3;
iv) Dodecanediol dimethacrylate (DDMA); and
v) Isobornyl methacrylate;
4) 0–20 weight-% of 2,2-bis(4-(2-hydroxy-3-methacryloyloxypropoxy)phenyl)propane (bis-GMA) and/or at least one ethoxylated bisphenol-A dimethacrylate,
5) 0–10 weight-% of at least one filler,
6) 0–1 weight-% of at least one photoinitiator system, and
7) 0–1 weight-% of at least one color pigment.

59. Dental kit according to claim 58, wherein the silicone has a Shore A hardness of 50 to 80.

60. Dental kit according to claim 58, wherein the silicone is a crosslinking vinyl polysiloxane.

61. Dental kit according to claim 58, wherein the composite is a photocrosslinking polymer filled with glass or organic fillers.

* * * * *

UNITED STATES PATENT AND TRADEMARK OFFICE
CERTIFICATE OF CORRECTION

PATENT NO.     : 6,426,373 B1
DATED          : July 30, 2002
INVENTOR(S)    : Frank Stange et al.

It is certified that error appears in the above-identified patent and that said Letters Patent is hereby corrected as shown below:

<u>Title page,</u>
Item [75], correct inventor(s) place of residence from:
    1st inventor change "Westerfelder" to -- Usingen, Germany --
    2nd inventor change "Schnurstrasse" to -- Bad Nauheim, Germany --
    3rd inventor change "Dietrich Bonhoefer" to -- Wehrheim, Germany --
    4th inventor change "Theodor-Heuss-Strasse" to -- Neu-Anspach, Germany --

Signed and Sealed this

Twenty-first Day of January, 2003

JAMES E. ROGAN
*Director of the United States Patent and Trademark Office*